(12) United States Patent
Brakenhielm et al.

(10) Patent No.: US 9,238,008 B2
(45) Date of Patent: Jan. 19, 2016

(54) PARTICLES CONTAINING A GROWTH FACTOR, AND USES THEREOF

(75) Inventors: Ebba Brakenhielm, Rouen (FR); Sébastien Banquet, Suresnes (FR); Florence Edwards-Levy, Reims (FR); Christian Thuillez, Rouen (FR)

(73) Assignees: Institut National de la Sante et da la Recherche Medicale (INSERM), Paris (FR); Centre National de la Recherche Scientifique (CNRS), Paris (FR); Universite de Rouen, Mont-Saint-Aignan (FR); Universite de Reims Champagne-Ardennes, Reims (FR); Centre Hospitalier Universitaire de Rouen, Rouen (FR)

( * ) Notice: Subject to any disclaimer, the term of this patent is extended or adjusted under 35 U.S.C. 154(b) by 0 days.

(21) Appl. No.: 14/002,435

(22) PCT Filed: Mar. 5, 2012

(86) PCT No.: PCT/EP2012/053733
§ 371 (c)(1),
(2), (4) Date: Aug. 30, 2013

(87) PCT Pub. No.: WO2012/119980
PCT Pub. Date: Sep. 13, 2012

(65) Prior Publication Data
US 2013/0337076 A1 Dec. 19, 2013

(30) Foreign Application Priority Data
Mar. 4, 2011 (EP) .................. 11305233

(51) Int. Cl.
*A61K 9/50* (2006.01)
*A61K 38/18* (2006.01)
*A61K 47/42* (2006.01)
*A61K 38/01* (2006.01)
*A61K 38/19* (2006.01)
*A61K 38/22* (2006.01)
*A61K 38/27* (2006.01)

(52) U.S. Cl.
CPC .............. *A61K 9/50* (2013.01); *A61K 9/5036* (2013.01); *A61K 38/012* (2013.01); *A61K 38/18* (2013.01); *A61K 38/1825* (2013.01); *A61K 38/1833* (2013.01); *A61K 38/1858* (2013.01); *A61K 38/1866* (2013.01); *A61K 38/19* (2013.01); *A61K 38/2264* (2013.01); *A61K 38/27* (2013.01); *A61K 47/42* (2013.01)

(58) Field of Classification Search
None
See application file for complete search history.

(56) References Cited

U.S. PATENT DOCUMENTS

| 5,550,178 | A | 8/1996 | Desai et al. | |
|---|---|---|---|---|
| 5,658,592 | A * | 8/1997 | Tanihara et al. | 424/488 |
| 8,153,591 | B2 * | 4/2012 | Masters et al. | 514/17.2 |
| 2003/0087985 | A1 | 5/2003 | Hubbell et al. | |
| 2009/0022805 | A1 * | 1/2009 | Slager et al. | 424/486 |

FOREIGN PATENT DOCUMENTS

| WO | 96/29998 A1 | 10/1996 |
|---|---|---|
| WO | 01/28524 A1 | 4/2001 |
| WO | 2005/034852 A2 | 4/2005 |
| WO | WO 2005/034852 * | 4/2005 |
| WO | 2009/005718 A1 | 1/2009 |

* cited by examiner

*Primary Examiner* — Jeffrey T Palenik
(74) *Attorney, Agent, or Firm* — Whitham Curtis Christofferson & Cook, PC (57) ABSTRACT

The present invention concerns particles containing at least one covalently cross-linked polysaccharide and at least one growth factor, a method of preparation, and uses thereof.

13 Claims, 6 Drawing Sheets

FIG.1 First part

FIG.1 Second part

FIG.1 Third and last part

PARTICLES CONTAINING A GROWTH FACTOR, AND USES THEREOF

The present invention relates to particles containing a growth factor, and uses thereof, in particular for the controlled spatiotemporal delivery of said growth factor.

It also relates to a method for preparing said particles.

Therapeutic delivery of growth factors has been attempted in clinical trials, for example in cardiovascular disease patients, but has not shown the expected functional benefits. One reason may be that the growth factors used to stimulate a response are rapidly degraded following injection into the circulation or in the target organ, and that the therapy thus is too short-lived to generate a durable result.

Thus, techniques allowing spatiotemporal control over growth factor release rates must be taken into consideration when developing novel therapeutic angiogenesis therapies, for example for cardiovascular disease patients.

In contrast to bolus delivery of proteins by systemic or local injections, delivery using slow-release delivery systems shows significantly improved efficacy by allowing a local and sustained release of growth factors at low doses (Richardson et al. Nat. Biotechnol. 19, 1029 (2001), A. H. Zisch et al. Cardiovasc. Pathol. 12, 295-310 (2003)).

Previous therapies based on polymer delivery of growth factors (C. Fischbach & D. J. Mooney Adv. Polym. Sci. 203, 191-221 (2006), Richardson et al. Nat. Biotechnol. 19, 1029 (2001), F-M Chen et al. Biomaterials 31, 6279-6308 (2010)) have used either non-injectable solid, implantable scaffolds, or injectable "gel like" formulations, resulting in a non-homogenous tissue distribution pattern of the growth factors and a poor duration of growth factor delivery.

Various particles, prepared from synthetic or natural biodegradable polymers or from proteins, have been studied for the encapsulation of growth factors.

Many studies deal with the use of microspheres composed of ionically cross-linked alginate as drug delivery systems for growth factors.

The aim of the present invention is to provide particles containing at least one growth factor, which allow a slow release of said growth factor.

The aim of the present invention is to provide particles able to provide a potent, localized and prolonged biological effect, such as a cellular growth, proliferation, differentiation and/or maturation.

The present invention relates to a particle containing at least one covalently cross-linked polysaccharide and at least one growth factor.

In the literature, methods for the preparation of particles made of covalently cross-linked polysaccharides can be found (U.S. Pat. No. 4,780,321, M C Lévy and M C Andry, Int. J. Pharm. 62, 27-35 (1990); R. Hurteaux et al., Eur. J. Pharm. Sci. 24, 187-197, 2005; M. Callewaert et al., Int. J. Pharm. 366, 103-110 (2009)). However, the use of these particles as delivery systems for growth factors is neither suggested nor described.

A study performed on calcium alginate microspheres surrounded with a polysaccharide-protein co-cross-linked membrane (M. Callewaert et al., Int. J. Pharm. 366, 103-110 (2009)) showed that a cationic bioactive peptide interacted with the internal ionically cross-linked alginate hydrogel, but did not engage interactions with the material constituting the polysaccharide-protein co-crosslinked membrane. Thus, the use of particles surrounded by a polysaccharide-protein co-crosslinked membrane but lacking the internal ionically cross-linked alginate hydrogel does not appear to a skilled man in the art to be adequate for the loading of growth factors.

Surprisingly, it was found that particles loaded with growth factors according to the invention, though lacking the internal ionically cross-linked alginate hydrogel, were able to release the loaded growth factors in a controlled and sustained manner.

The particles of the invention are able to provide a slow release of said growth factor and the biological effects are of longer duration as compared to growth factor delivery with particles without such covalently cross-linked polysaccharide.

The particles of the invention are able to provide a release of said growth factors on a period of at least 15 days, and generally on a period of approximately 40 days.

The use of particles as vectors for growth factors brings the advantage of dividing the dose into discrete drug delivery systems that can spread over a local territory to infuse the therapeutic molecules more homogeneously, providing a more physiological-like stimulation. Moreover, these particles are also intended to protect the bioactive peptides until they reach their biological target.

Such particles are particularly advantageous for homogenous concentration gradients of growth factors inside target organs, for example for therapeutic stimulation of blood vessel growth (i.e. angiogenesis and arteriogenesis), for stimulating wound healing, for tissue regeneration in vivo or for stimulating transplant organ grafting.

Slow release of growth factors thus induces biological effects. The stabilization of those effects is permitted by the extended duration of such release.

As used herein, the term "particle" refers to an aggregated physical unit of solid material.

The particles according to the invention are preferably microparticles.

Microparticles are herein understood as particles having a median diameter $d_{50}$ less than 1 000 µm.

As used herein, the term "median diameter $d_{50}$" refer to the particle diameter so that 50% of the volume of the particles population have a smaller diameter.

The median diameter $d_{50}$ according to the invention is determined by virtue of a particle size measurement performed on the suspensions according to the method based on light diffraction.

In a particular embodiment, a particle according to the invention, also called microcapsule, preferably presents a core/shell structure, also called a core/membrane structure. The cross-linked polysaccharide is preferably comprised at least in the shell of the particle. Advantageously, the shell of the particle is solid and consists essentially in the cross-linked polysaccharide.

The core of such particles may be solid, liquid or gaseous, but may not be an ionically cross-linked hydrogel.

The solid core of the particles may consist in various material particles, like polymer, metal, mineral.

The gaseous core of the particles may consist in various gases, like air, nitrogen or argon.

According to one embodiment, the core of the particles is liquid.

In one embodiment, a particle according to the invention presents a core/membrane structure, wherein:
the membrane comprises at least one covalently cross-linked polysaccharide and at least one growth factor, and
the core is liquid.

According to another embodiment, a particle according to the invention presents a core/membrane structure, wherein:
the membrane consists in a covalently cross-linked polysaccharide, on which at least one growth factor is adsorbed, and the core is liquid.

The membrane generally does not comprise ionically cross-linked polysaccharide, such as coacervates of polysaccharides.

In another particular embodiment, a particle according to the invention presents a matrix structure, formed of a network comprising at least one covalently cross-linked polysaccharide.

Said particle is also called microsphere. The network of said particle fills the whole volume of the particle. Advantageously, said network is solid. Said particle may contain a liquid filling the pores of said network. Said particle may also contain gas bubbles or solid particles.

In another embodiment, a particle according to the invention presents a matrix structure, wherein:
the constitutive network comprises at least one covalently cross-linked polysaccharide and at least one growth factor adsorbed on it, and
the network entraps an aqueous solution in its pores.

The median diameter $d_{50}$ of the particles according to the invention is preferably comprised from 5 μm to 1 000 μm, more preferably from 50 μm to 200 μm, more preferably from 75 μm to 150 μm, and more preferably from 60 μm to 100 μm.

As used herein, the term "polysaccharide" refers to polymeric carbohydrate structures, formed of repeating units joined together by glycosidic bonds. These structures are often linear, but may contain various degrees of branching. The term "polysaccharide" refers to a single polysaccharide or a mixture of two or more polysaccharides.

As used herein, the terms "covalently cross-linked polysaccharide" refer to a polymer formed of polysaccharide units, linked together by covalent chemical bonds. Such bonds generally bind together two polymer chains of two polysaccharide molecules. Alternatively, such bonds can bind together the same polysaccharide molecule, thus forming a loop-shaped pattern.

Such covalently cross-linked polysaccharide is usually obtained from a polysaccharide, or a mixture of two or more different polysaccharides, treated in the presence of a cross-linking agent or using another method leading to the formation of covalent cross-links between the polysaccharide molecules.

A method for the preparation of said covalently cross-linked polysaccharides will be further described.

The polysaccharide of the particle according to the invention is preferably chosen from the group consisting of gum Arabic, xanthan gum, gellan gum, acacia gum, tragacanth gum, guar gum, carob gum, karaya gum, alginic acid and derivatives thereof, alginic salts, alginic esters like propylene glycol alginate, pectins, algal sulfated polysaccharides like sulfated fucans and galactans, agars, carrageenans, fucoidans, gluco- and galactomannans, arabinogalactans, glycosaminoglycans like hyaluronic acid, dermatan-sulfate, keratan-sulfate and degradation products thereof, chondroitin-4-sulfate, chondroitin-6-sulfate, heparan-sulfate, heparin and derivatives thereof, pentosans, dextrans, chitosan and derivatives thereof, hydrosoluble and hydrodispersible derivatives of starch or cellulose like starch or cellulose alkylethers, hydroxyalkylethers or carboxyethylethers, like carboxymethylstarches, hydroxyethylstarches, carboxymethylcelluloses, and mixtures thereof.

Advantageously, the polysaccharide of the particle according to the invention possesses an affinity for the growth factor of the particle, and is preferably negatively-charged.

The polysaccharide of the particle according to the invention is more advantageously selected from the group consisting of gum Arabic, alginic acid and derivatives thereof, alginic salts, alginic esters, algal sulfated polysaccharides like sulfated fucans and galactans, agars, carrageenans, fucoidans, glycosaminoglycans like hyaluronic acid and degradation products thereof, chondroitin-4-sulfate, chondroitin-6-sulfate, dermatan-sulfate, keratan-sulfate, heparan-sulfate, heparin and derivatives thereof, and mixtures thereof.

Gum Arabic is also called acacia gum.

Alginic acid derivatives are preferably salts of alginic acid, such as salts of monovalent cation like sodium, lithium or potassium, preferably sodium.

Other preferred alginic acid derivatives are esters of alginic acid, where some of the carboxyl groups are esterified with a hydroxyl containing compound, such as an alcohol or glycol, like ethylene glycol, propylene glycol, glycerol, preferably propylene glycol.

According to one embodiment, the membrane of the particles according to the invention consists in a covalently cross-linked polysaccharide, on which at least one growth factor is adsorbed.

According to one embodiment, the polysaccharide of the particle according to the invention is chosen from the group consisting in alginic acid derivatives, gum Arabic, carrageenans, and chondroitin-sulfates.

According to one embodiment, the particle according to the invention further comprises a protein which is co-cross-linked with the polysaccharide.

As used herein, the term "co-cross-linked" refers to a protein bound to the polysaccharide polymer, preferably by covalent bonds. The cross-linking of the protein may occur after, or during the cross-linking of the polysaccharide molecules.

According to another embodiment, a particle according to the invention presents a core/membrane structure, wherein:
the membrane consists in a covalently cross-linked polysaccharide co-cross-linked with a protein, on which at least one growth factor is adsorbed, and
the core is liquid.

Said protein is preferably chosen from the group consisting of albumins like serumalbumin, ovalbumin or alpha-lactalbumin, globulins, solubilized scleroproteins, collagen, atelocollagen, gelatin, elastin, hemoglobin, fibrinogen, fibrin, silk fibroin, milk proteins, casein, glycoproteins like fibronectin or mucin, plant proteins extracted from a leguminous or proteagenous plant, plant proteins extracted from a cereal, and mixtures thereof.

According to one embodiment, the protein of the particle according to the invention is an albumin-type protein, such as serum-albumin, and is for example human serum albumin (HSA).

As used herein, the term "growth factor" refers to a naturally occurring substance capable of stimulating cellular growth, cellular proliferation, cellular differentiation and cellular maturation, such as, for example, bone cell differentiation or blood vessel differentiation.

According to one embodiment, the growth factor is adsorbed to the covalently cross-linked polysaccharide comprised in the membrane or the whole volume of the particle according to the invention.

Advantageously, said covalently cross-linked polysaccharide forms a network and the growth factor is bound to the said network, preferably by electrostatic interactions.

According to another embodiment, the membrane of the particles according to the invention consists in a covalently cross-linked polysaccharide, co-cross-linked with a protein, on which at least one growth factor is adsorbed.

A particle according to this embodiment comprises propylene glycol alginate as cross-linked polysaccharide, and human serum albumin as protein co-cross-linked with the polysaccharide.

Another particle according to this embodiment comprises covalently cross-linked gum Arabic, co-cross-linked with human serum albumin.

Another particle according to this embodiment comprises covalently cross-linked chondroitin-sulfate, co-cross-linked with human serum albumin.

Another particle according to this embodiment comprises propylene glycol alginate and sodium alginate as cross-linked polysaccharides, and human serum albumin as protein co-cross-linked with the polysaccharides.

According to one embodiment, the particle according to the invention comprises at least two growth factors.

The particles according to this embodiment preferably comprise two different growth factors.

Such particles enable the controlled spatiotemporal delivery of different growth factors, which induce different therapeutic effects according to different kinetics of release. It has been observed that such particles synergistically enhance the therapeutic effects of each growth factor.

According to this embodiment, it is preferable to select the nature of the particles in order to adjust the kinetics of release of each growth factor.

According to this embodiment, it is also preferable to associate on the same particle, two growth factors with shifted kinetics of release.

According to one embodiment, the membrane of the particles according to the invention consists in a covalently cross-linked polysaccharide, on which at least two growth factors are adsorbed.

According to this embodiment, the membrane of the particles consists in covalently cross-linked propylene glycol alginate, gum Arabic, carrageenan, or chondroitin-sulfate.

According to another embodiment, the membrane of the particles according to the invention consists in a covalently cross-linked polysaccharide, co-cross-linked with a protein, on which at least two growth factors are adsorbed.

A particle according to this embodiment comprises propylene glycol alginate as cross-linked polysaccharide, and human serum albumin as protein co-cross-linked with the polysaccharide.

Another particle according to this embodiment comprises covalently cross-linked gum Arabic, co-cross-linked with human serum albumin.

Another particle according to this embodiment comprises covalently cross-linked chondroitin-sulfate, co-cross-linked with human serum albumin.

Another particle according to this embodiment comprises propylene glycol alginate and sodium alginate as cross-linked polysaccharides, and human serum albumin as protein co-cross-linked with the polysaccharides.

In the particles according to the present invention, the species that form the membrane (polysaccharides and eventual proteins) are essentially covalently cross-linked, thus leaving the negatively-charged sites of the membrane fully available to interact with the growth factors, notably with their positively-charged sites.

On the contrary, in an ionically cross-linked particle, most of the polarized sites of the membrane are already engaged in an ionic bond with another site of opposite polarity. Those sites are thus less available and such particles exhibit a weaker affinity with growth factors.

Furthermore, proteins comprise various functional groups able to bind molecules through ionic or hydrophobic interactions. The presence of a co-cross-linked protein in the membrane of the particles of the invention brings additional binding sites for the growth factors, allowing a modulation of their release.

The growth factor of the particle according to the invention is chosen from the group consisting of fibroblast growth factors (FGFs), hepatocyte growth factor (HGF), platelet derived growth factors (PDGFs), vascular endothelial growth factors (VEGFs), angiopoietins (Angs), granulocyte colony-stimulating factor (GCSF), transforming growth factors (TGFs), placental growth factors (PlGFs), epidermal growth factor (EGF), stromal derived growth factor (SDF-1), insulin-like growth factors (IGFs), nerve growth factor (NGF), osteogenin, or hormones such as leptin, growth hormone (GH), estrogen, or cytokines such as interleukins 1, 6, or 8, and mixtures thereof.

In one embodiment, the growth factor of the particle according to the invention is preferably chosen from the group consisting of FGF-2, HGF, PDGF-BB and VEGF-A.

In one embodiment, the particle according to the invention comprises two different growth factors. Preferably, the particle according to the invention comprises HGF and FGF-2 as growth factors. Preferably, the particle according to the invention comprises PDGF-BB and FGF-2 as growth factors.

In another embodiment, the particle according to the invention comprises more than two different growth factors.

The particle according to the invention is a growth factor delivery system capable of delivering growth factor combinations with different kinetics, producing synergistic effects.

Within the present invention, it was found that polysaccharides are suitable for the delivery of growth factor(s).

Within the present invention, it was found that alginate, a naturally occurring polysaccharide, is particularly suitable for the delivery of positively charged proteins, such as FGF-2, HGF, VEGF-A and PDGF-BB, as it bears negatively charged carboxylic groups available for electrostatic interactions with the positively charged growth factors, thus slowing their release.

In addition, it was found that human serum albumin, a biocompatible and biodegradable protein, brings enhanced mechanical resistance to the particle network, and influences the release kinetics of the growth factors.

Indeed, ionically cross-linked alginate hydrogels have been widely used for angiogenic growth factor delivery (Ruvinov et al. Biomaterials 31, 4573 (2010); Hao et al. Cardiovascular Research 75, 178 (2007)), but generally display uncontrolled degradation leading to unpredictable release kinetics.

In contrast, the particles of the invention comprising covalently cross-linked polysaccharide and particles further comprising proteins co-cross-linked to the polysaccharide prevent hydrolysis-driven dissolution and delay proteases-driven degradation resulting in more stable particles with reproducible drug release rates.

Particles composed of cross-linked anionic polysaccharides, such as alginate, and eventually co-cross-linked proteins, such as HSA, thus can be used to control the release of many different growth factors. Furthermore, the association of polysaccharides to proteins in a cross-linked network delays the degradation of the particles by proteases, which is very useful for the encapsulation of growth factors with short half-lives.

Another particle according to the invention comprises chondroitin-sulfate as cross-linked polysaccharide, and human serum albumin as protein co-cross-linked with the polysaccharide.

This natural glycosaminoglycan (chondroitin-sulfate) is likely to bind more specifically heparin-binding growth factors, and allows the encapsulation of more growth factors for an even longer period of delivery.

The particles according to the invention are stable, biocompatible and biodegradable.

Because of the strong covalent bonds maintaining their membrane, the covalently cross-linked particles according to the invention are more stable than the ionically cross-linked particles of prior art.

The particles according to the invention are injectable, allowing spatiotemporal control over growth factor levels, and represent a less invasive delivery system than implantable delivery systems.

They are also a more potent delivery system for growth factors, and are therefore of clinical interest, for example for the treatment of cardiovascular disease patients, for the treatment of degenerative diseases, for the treatment of skin conditions related to aging, or for tissue engineering of in vitro cell culture.

The particles according to the invention are discrete particles, which can disperse independently into the tissue during their administration, leading to favourable concentration gradients, and avoiding the problems associated with too high local doses, including angioma formation or aberrant dysfunctional blood vessels.

Indeed, it was discovered that it is not the total amount of growth factor(s) that determines the results of treatment, but rather that local, microenvironmental concentration gradients play an important role (Ozawa et al, J. Clin. Invest. 2004, 113(4), 516-527).

The particles according to the invention allow better tissue distribution of the growth factors around the site of injection.

The particles according to the invention also prevent undesired wide-spread distribution of growth factors inside the target organ or into the circulation.

Their slow-release property also allows the reduction in the required dose to reach a certain biological effect, by enhancing the half-life of the growth factors and by protecting them from proteolysis. This results in reducing costs for the treatment but also importantly leads to a significantly reduced risk of serious side effects from the treatment.

In a further aspect, the invention is directed to a method of preparation of the particles according to the invention, comprising a step of covalently cross-linking a polysaccharide, in order to provide particles containing at least one covalently cross-linked polysaccharide.

The step of cross-linking of the method according to the invention is typically carried out by a method chosen from the group comprising interfacial cross-linking using acid dichlorides or acid dianhydrides, cross-linking using a transacylation reaction between a polysaccharidic ester and a protein or a polysaccharide, cross-linking by aldehydes or polyaldehydes, diisocyanates, diacrylates, carbodiimides, trisodium trimetaphosphate, diglycidylethers, epichlorohydrin, radiation cross-linking induced by electron beam or gamma rays exposure, photocross-linking, enzymatic cross-linking.

Alternatively, the step of cross-linking may be carried out by any other method allowing the formation of covalent bonds between the polysaccharide molecules, at least on the surface of an aqueous droplet, in order to provide particles containing at least one covalently cross-linked polysaccharide.

A first method for the step of cross-linking is interfacial cross-linking using acid dichlorides like terephthaloyl chloride, sebacoyl chloride, succinyl chloride, glutaryl chloride or adipoyl chloride.

The following protocol illustrates this first method.

An aqueous solution of the polysaccharide, or mixture of polysaccharide, is divided in small droplets, by emulsification in a hydrophobic liquid added with surfactant. A solution of the acid dichloride in the same hydrophobic liquid is then added to the emulsion. The acid dichloride diffuses through the emulsion and binds the functional groups of the polysaccharide at the surface of the aqueous droplets through an acylation reaction, leading to the appearance of cross-links between polysaccharides when the binding of the bifunctional cross-linking agent occurs on two different polysaccharide molecules. The acylation reaction may concern hydroxyl groups, amino groups, carboxylic acid groups, of the polysaccharide, leading to the formation of ester bonds, amide bonds, and anhydride bonds, respectively. A membrane made of cross-linked polymer is progressively formed around each aqueous droplet, leading to the individualization of microcapsules. The reaction is stopped by diluting the emulsion with organic solvent. The particles are separated from the reaction medium by centrifugation, and subjected to a series of washings in order to eliminate solvent and surfactant residues.

Another method for the step of cross-linking is cross-linking using a transacylation reaction between a polysaccharidic ester like propylene glycol alginate or pectin and a protein or a polysaccharide.

The following protocol illustrates this other method.

In this method, an aqueous solution containing protein, for example albumin, and polysaccharide, for example propylene glycol alginate (PGA), is divided in small droplets, by emulsification in a hydrophobic liquid added with surfactant. A solution of an alkaline agent like diluted sodium hydroxide solution is then added to the emulsion. The alkaline agent diffuses through the emulsion and starts the transacylation reaction between ester groups of polysaccharide and amino groups of the protein, leading to the appearance of amide cross-links between the two molecules. A membrane made of cross-linked polysaccharide and protein is progressively formed around each aqueous droplet, leading to the initial individualization of microcapsules. When the reaction progresses towards the center of each aqueous droplet, the network made of cross-linked protein and polysaccharide progresses up to the center as well, leading to the formation of microspheres. The reaction is stopped by adding an acidic solution to the emulsion. The particles are separated from the reaction medium by centrifugation, and subjected to a series of washings in order to eliminate solvent and surfactant residues.

According to one embodiment, the method of preparation of the particles according to the invention further comprises a step of imbibition of the particles containing at least one covalently cross-linked polysaccharide, with a solution containing at least one growth factor.

Said step of imbibition is preferably carried out after the step of cross-linking.

As used herein, the terms "loaded particles" refer to particles obtained after the step of imbibition with a growth factor.

In the embodiment wherein the particles present a liquid core, the growth factors may be bound to the membrane of the loaded particles and may also be present in the solution forming the liquid core of the loaded particles.

In another embodiment wherein the particles present a matrix structure, the growth factors may be bound to the network constituting the loaded particles and may also be present in the solution filling the pores of the network constituting the loaded particles.

Lyophilized particles are loaded with one or more growth factors (for example HGF, FGF-2, PDGF-BB, and VEGF-A) by imbibition, using solutions of said growth factors, in order to provide loaded particles, said solutions containing one or more growth factors.

In one embodiment, two (or more) fractions of the particle batch are separated and separately loaded with different growth factors before being associated in a composition, particularly in an injectable pharmaceutical composition. This method allows a great versatility to precisely adjust the proportions and the loading of the different fractions, depending on the desired sequential release kinetics.

According to one embodiment, the method of preparation of the particles according to the invention further comprises a step of lyophilization of the particles.

Said step of lyophilization of the particles is preferably carried out after the step of cross-linking and before the step of imbibition.

The method of preparation of the particles is very versatile and a skilled man in the art can adapt this method to the preparation of particles within a large size range and having various degrees of cross-linking.

The following protocol illustrates the formation of particles by the method of interfacial cross-linking.

A protein and a polysaccharide, for example human serum albumin and propylene glycol alginate, are dissolved in an aqueous phase. This aqueous phase is emulsified by stirring in an organic phase containing a surfactant. Then, an organic solution of acid dichloride is added to the emulsion and the cross-linking reaction is allowed to develop.

The reaction is stopped by dilution of the reaction medium. The particles are separated from the organic phase by centrifugation, and washed.

Finally, the particles are freeze-dried by lyophilisation.

Lyophilized particles are loaded with one or more growth factors (for example HGF, FGF-2, PDGF-BB and/or VEGF) by imbibition, using solutions of said growth factors, in order to provide loaded particles, said solutions containing at least one growth factor.

In one embodiment, said step of imbibition is separately conducted with two or more fractions of particles, using two or more solutions of growth factors.

In a further aspect, the invention is directed to the use of the particles according to the invention for the controlled spatiotemporal delivery of at least one growth factor.

In another aspect, the invention is directed to the particles according to the invention for the delivery of at least one growth factor to cultured cells in vitro for tissue engineering.

In another aspect, the invention also relates to the particles according to the invention for their use for stimulating wound healing such as in ischemic skin wounds, diabetic ulcers, gastric ulcers, or in burn wounds, or for tissue regeneration in vivo, like therapeutic angiogenesis, bone regeneration, nerve regeneration, muscle regeneration, regeneration of hepatic tissue, regeneration of hybrid tissue apparatus like periodontium, or for stimulating transplant organ grafting.

In another aspect, the invention also relates to the particles according to the invention for their use for the treatment of cardiovascular diseases like ischemic heart disease, chronic heart failure, limb ischemia or cerebral ischemia.

In another aspect, the invention also relates to the particles according to the invention for their use for the treatment of lymphedema by stimulation of lymphangiogenesis.

In another aspect, the invention also relates to the particles according to the invention for their use for the treatment of degenerative diseases like osteoarthritis, osteonecrosis, osteoporosis or periodontitis, or neurodegenerative diseases such as alzheimers.

In another aspect, the invention also relates to the particles according to the invention for their use for the treatment of skin changes related to aging.

In a further aspect, the invention is directed to a pharmaceutical composition comprising particles according to the invention, in association with a pharmaceutically acceptable vehicle.

In a further aspect, the invention relates to a pharmaceutical composition comprising n series of particles according to the invention, in association with a pharmaceutically acceptable vehicle, each of said series of particles being loaded with a different growth factor, n being 2, 3, 4 or more.

According to one embodiment, the pharmaceutical composition of the invention comprises a first series and a second series of particles according to the invention, wherein the first series of particles is loaded with a first growth factor and the second series of particles is loaded with a second growth factor, wherein the second growth factor is different from the first growth factor.

Such pharmaceutical composition enables the controlled spatiotemporal delivery of different growth factors, which induce different therapeutic effects according to different kinetics of release. It has been observed that such pharmaceutical composition synergistically enhance the therapeutic effects of each growth factor.

According to this embodiment, it is preferable to select the nature of the particles in order to adjust the kinetics of release of each growth factor.

According to this embodiment, it is also preferable to associate in the same pharmaceutical composition, two growth factors with shifted kinetics of release.

FIGURES

Particles have a mean diameter of 100 μm as observed by granulometry.

The migration of HMEC-C (FIG. 2a), HME (FIG. 2b), and SMC (FIG. 2c) is assayed in Boyden chambers for 6 hours.

Cells, pretreated or not with FGF-2 or HGF, were stimulated or not with HGF or FGF-2.

FIG. 3a represents the proliferation of FGF-2-pretreated HMEC-C cells stimulated or not with HGF.

FIG. 3b represents the proliferation of FGF-2-pretreated HME cells stimulated or not with HGF.

FIG. 3c represents the proliferation of HGF-pretreated SMCs, stimulated or not with FGF-2.

FIG. 3d represents the proliferation of HGF-pretreated HMEC-C cells stimulated or not with FGF-2.

Proliferation data is presented as fold increase over initial cell numbers (mean±SEM, n=6 per group). *P<0.05; P<0.01; *P<0.001.

Vessel formation, induced by microcapsule delivery of FGF-2 and/or HGF, was analyzed in Matrigel plugs in mice by immunohistochemical double labeling for CD31 (FIG. 4a) and αSMA (FIG. 4b).

Vascular density (FIG. 4a) and mature vessel density (FIG. 4b), quantified at 10×, is reported as the number of CD31$^+$ and SMA$^+$ vessels per mm$^2$, respectively. Plug vessel content, quantified at 2.5×, is presented as percentage vascularized area to the total area of the section (FIG. 4c).

Data is presented as mean determinants (±SEM; n=5 mice per group). *P<0.05; P<0.01; *P<0.001.

EXAMPLES

Preparation and Characterization of the Particles

Example 1

Preparation of Growth Factor-Loaded Albumin-Alginate Particles Using Interfacial Cross-Linking Method Albumin-alginate particles can be prepared according to the following method of interfacial cross-linking.

4% (w/v) human serum albumin (HSA, LFB) and 2% (w/v) propylene glycol alginate (PGA, ISP) are dissolved in a phosphate buffer pH 7.4. This aqueous phase is emulsified in cyclohexane (SDF) containing 2% (w/v) sorbitan trioleate (Sigma), at a stirring speed of 2000 rpm. Then, a 2.5% (w/v) solution of terephthaloyl chloride (Acros) in a chloroform-cyclohexane (1:4 v/v) mixture is added to the emulsion and the cross-linking reaction is allowed to develop for 30 min.

The reaction is stopped by dilution of the reaction medium. The particles are separated from the organic phase by centrifugation, and washed successively with cyclohexane, with ethanol (Charbonneaux-Brabant) containing 2% (w/v) polysorbate (Sigma), with 95% (v/v) ethanol and finally thrice with pure water.

Diameter measurements are performed using laser diffraction (Particle Sizer LS200, Beckman-Coulter). After staining with methylene blue, the particles can be observed with a light microscope (Olympus, BH-2) equipped with interferential phase contrast. SEM observations (JSM-5400LV, JEOL) can be made after alcohol dehydration of particle suspension followed by Au/Pd coating. Finally, the particles are freeze-dried by lyophilisation in a Freezone 6 (LabConco, condenser temperature: −45° C., pressure <0.5 mbar).

Lyophilized particles are loaded with growth factors (HGF, FGF-2 and/or PDGF-BB) by imbibition, using 0.5-2 µg growth factor per mg particles (approximately 35,000 particles), during a 1 h-1 h30 incubation at +4° C.

Figure 1:
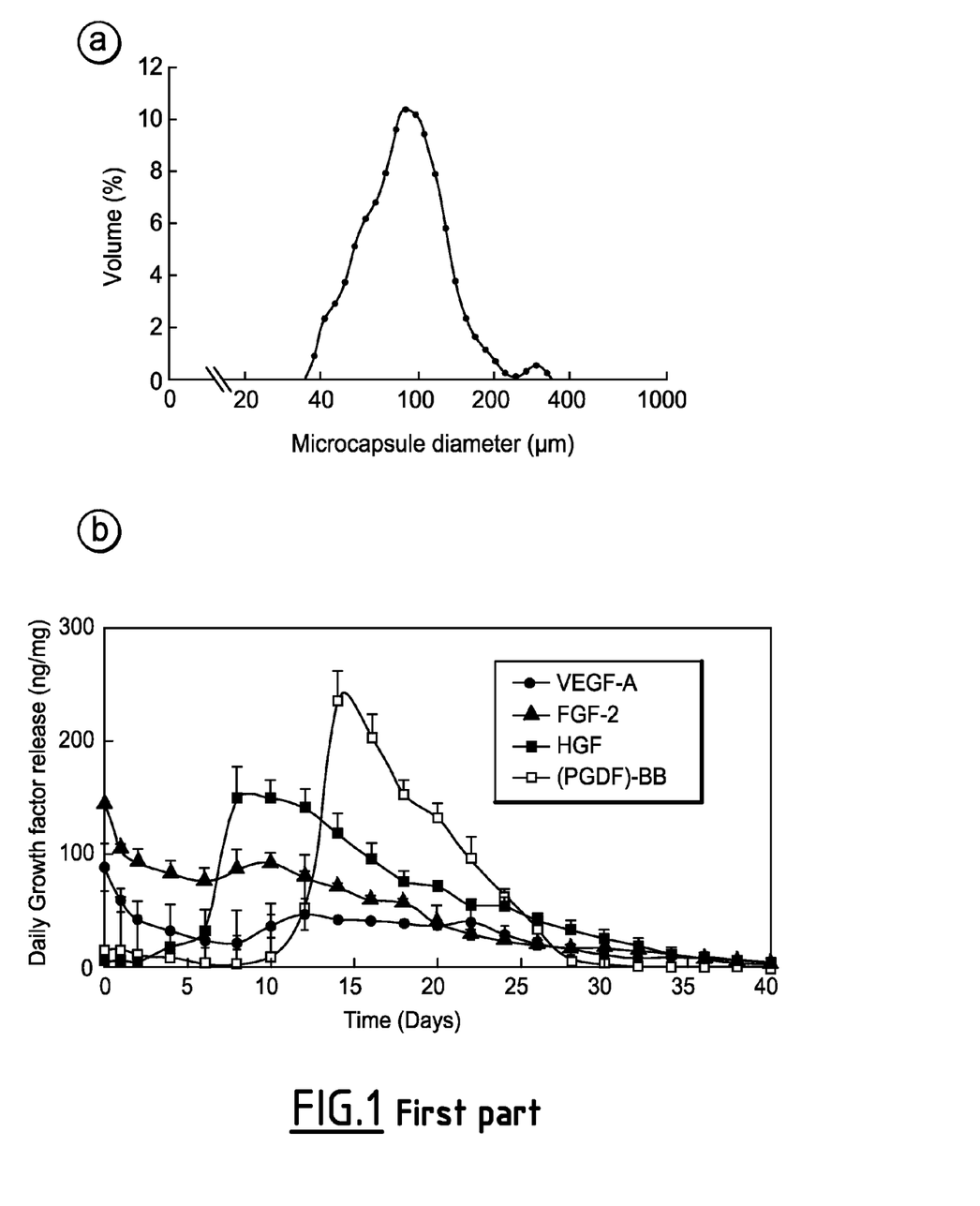
FIG. 1a represents the distribution of size of albumin-alginate particles of Example 1.
FIG. 1b represents in vitro growth factor release rate of albumin-alginate particles of Example 1, loaded with FGF-2 (triangle), HGF (black square), PDGF-BB (white square) or VEGF-A (black dots), evaluated every other day for 6 weeks. Amounts are given as ng growth factor released per day per mg of particles.
FIG. 1c represents in vitro growth factor release rate of VEGF-A by albumin-gum Arabic particles of Example 2 (black square), carrageenan particles of Example 3 (white triangle), chondroitin particles of Example 3 (white dots) and albumin-chondroitin particles of Example 2 (white square), loaded with VEGF-A. Amounts are given as ng growth factor released per mg of particles per day.
FIG. 1d represents in vitro growth factor release rate of HGF by albumin-alginate particles of Example 1 (black square) or alginate particles of Example 3 (white dots), loaded with HGF. Amounts are given as ng growth factor released per mg of particles per day.
FIG. 1e represents in vitro growth factor release of VEGF by albumin-alginate particles of Example 1 prepared by interfacial cross-linking method (black square) or albumin-alginate particles of Example 6 prepared by transacylation method (white dots), loaded with VEGF. Amounts are given as ng growth factor released per mg of particles per day.

The particles of Example 1 contain a thin, covalently cross-linked human serum albumin (HSA) and propylene glycol alginate (PGA) membrane surrounding a liquid center. Laser diffraction measurements and microscopic observations revealed that these albumin-alginate particles had a mean diameter of 100 µm and were roughly spherical (FIG. 1a). Dehydration caused a partial and reversible collapse, resulting in the appearance of a very pleated surface in desiccated particles as observed by scanning electron microscopy.

Example 2

Preparation of Particles by Interfacial Cross-Linking of Various Polysaccharides Associated to Human Serum Albumin The procedure described in Example 1 can be used to prepare particles from the association of human serum albumin (HSA) to other polysaccharides using an interfacial crosslinking procedure.

The preparation parameters which differ from those of Example 1 are presented in the table below.

| Preparation of the aqueous solution | Terephthaloyl chloride concentration in the chloroform-cyclohexane (1:4 v/v) mixture |
|---|---|
| Sodium alginate (Sigma, 2% m/V) and HSA (LFB, 4% m/V) in Phosphate buffer, pH 7.4 | 2.5% m/V |
| Gum Arabic (Spraygum AB, CNI, 20% m/V) and HSA (4% m/V) in Phosphate buffer, pH 7.4 | 2.5% m/V |
| Chondroïtin sulfate (Sigma, 10% m/V) and HSA (4% m/V) in NaOH 0.1N | 5% m/V |

The particles are then washed, lyophilized and loaded with growth factors as described in Example 1.

Laser diffraction measurements and microscopic observations revealed that the particles of sodium alginate/HSA, gum Arabic/HSA, and chondroïtin sulfate had a mean diameter (+/−SD) of 86.02 (+/−44.34) µm, 68.38 (+/−20.92) µm, and 101.9 (+/−38.91) µm respectively, and were roughly spherical.

Example 3

Preparation of Particles by Interfacial Cross-Linking of Various Polysaccharides without the Addition of a Protein The procedure described in Example 1 can be used to prepare particles from various polysaccharides using an interfacial cross-linking procedure without the addition of a protein.

The preparation parameters which differ from those of example 1 are presented in the table below.

| Preparation of the aqueous solution | Emulsification step: stirring speed and organic phase | Terephthaloyl chloride concentration in the chloroform-cyclohexane (1:4 v/v) mixture |
|---|---|---|
| Propylene glycol alginate (Profoam, FMC Biopolymer) 5% m/V in NaOH 1N | 4000 rpm in Cyclohexane + 1% (m/V) sorbitan trioleate | 2.5% m/V |
| Sodium alginate (Sigma) 3% m/V in NaOH 1N | 4000 rpm in Cyclohexane + 1% (m/V) sorbitan trioleate | 2.5% m/V |
| Gum Arabic (Spraygum AB, CNI) 10% m/V in NaOH 1N | 1500 rpm in Cyclohexane + 2% (m/V) sorbitan trioleate | 2.5% m/V |
| Carrageenan (Sigma) 2% m/V in NaOH 1N at 60° C. | 2800 rpm in Cyclohexane + 2% (m/V) sorbitan trioleate | 2.5% m/V |
| Chondroïtin sulfate (Sigma) 10% m/V in NaOH 1N | 3500 rpm in Cyclohexane + 2% (m/V) sorbitan trioleate | 5% m/V |

The particles are then washed, lyophilized and loaded with growth factors as described in Example 1.

Laser diffraction measurements and microscopic observations revealed that the particles of propylene glycol alginate, gum Arabic, and chondroïtin sulfate had a mean diameter (+/−SD) of 73.48 (+/−42.38) μm, 63.86 (+/−35.21) μm, and 101.3 (+/−69.26) μm respectively, and were roughly spherical.

Example 4

Preparation of Growth Factor-Loaded Albumin-Alginate Particles Using the Transacylation Method The aqueous phase is prepared by dissolving 2% (m/V) PGA (Profoam, FMC Biopolymer) and 20% (m/V) HSA (LFB) in distilled water. 6 mL of this aqueous solution are then emulsified in 40 mL of isopropyl myristate (SDF) supplemented with 5% (m/V) sorbitan trioleate (Sigma) at a stirring speed of 3000 rpm. After 5 minutes of stirring, 2 mL of a 2% (MN) solution of sodium hydroxide in ethanol 95% (V/V) (Charbonneaux Brabant) are added to the emulsion. The emulsion is neutralized after 15 minutes by adding 2 mL of an 8.5 (V/V) solution of acetic acid in ethanol 95% (V/V). The agitation is stopped after 15 minutes. The particles are then separated from the reaction medium by centrifugation, and the pellet is then resuspended in a 2% (m/V) aqueous solution of polysorbate (Seppic) and thrice in pure water.

The particles are then lyophilized and loaded with growth factors as described in Example 1.

Laser diffraction measurements and microscopic observations revealed that the particles of propylene glycol alginate/HSA had a mean diameter (+/−SD) of 92.23 (+/−47.36) μm and were roughly spherical.

Example 5

Preparation of a Composition Containing Two Fractions of Particles Separately Loaded with Two Growth Factors for Sequential Prolonged Release In Vivo Growth factors stock solutions (about 100 ng/μl) are prepared as suggested by the manufacturer in PBS or $H_2O$ depending on the specific growth factor. Stock solutions are stored at −80° C. until usage. A defined amount of particles in an Eppendorf tube are loaded with one growth factor at the dose of 1 μg growth factor per mg particles (corresponding to about 35 000 particles). The total volume for the loading is kept at about 15-20 μL per mg particles (adjusted by addition of the release buffer, RB). The particles are incubated on ice for 1.5 h. Release buffer is then added to prepare a suspension for injection or for analyses of growth factor release.

For in vivo administration the following suspensions were prepared:
FGF-2 alone: ratio polymer/release buffer mg/mL 7,246
HGF alone: ratio polymer/release buffer mg/mL 1,812

In each case, 23 μL of this solution were injected in three spots of the left ventricle of rats making the total dose per heart 500 ng FGF2 or 125 ng HGF.
FGF-2 for combination: ratio polymer/release buffer mg/mL 10,417
HGF for combination: ratio polymer/release buffer mg/mL 5,952

16 μL of FGF-2-loaded particle suspension were mixed with 7 μL of the HGF-loaded particle suspension, and 23 μL of this mixed suspension was injected in three spots of the left ventricle making the total dose per heart 500 ng FGF-2+125 ng HGF.

For studies in mice, particles were charged at 1 or 2 μg growth factor per mg particles and the following solutions were prepared for injection in the in vivo matrigel model:
PDGF-BB alone: ratio polymer/release buffer mg/mL 10.0
VEGF-A alone: ratio polymer/release buffer mg/mL 10.0
HGF for combination: ratio polymer/release buffer mg/mL 6.897
FGF-2 for combination: ratio polymer/release buffer mg/mL 6.897

31 μL of FGF-2-loaded particle suspension were mixed with 8 μL of the HGF-loaded particle suspension, and 40 μL of this mixed suspension was injected in four spots in the left ventricle making the total dose per heart 500 ng FGF-2 or 125 ng HGF.

Example 6

Growth Factor Release Kinetics from Various Particles

The particles of Example 1 sequentially release FGF-2, HGF, PDGF-BB, or VEGF-A during more than 1 month, significantly increasing their angiogenic effects in vivo.

In order to achieve spatiotemporally-controlled release of angiogenic growth factors, injectable, particulate delivery systems are used.

The growth factor-loaded particles are resuspended at 4 mg particles/mL in extracellular fluid mimetic release buffer (EFM-RB; 5 mM KCl, 125 mM NaCl, 20 mM Hepes, 1.5 mM MgCl2, 1.5 mM CaCl2, pH 7.4) and incubated under continuous rotation (6 rpm) for 40 days at 37° C. Every other day the tubes are centrifuged (300 g, 8 min) to pellet the particles. A sample of the supernatant is collected and stored at −80° C. The initial volume in the test tube is restored by addition of fresh EFM-RB to simulate unlimited diffusion conditions. The growth factor-release is quantified by ELISA according to the manufacturer's instructions (VEGF-A, HGF and PDGF-BB, RnD systems; FGF-2, Invitrogen). Data are presented as mean amount (ng) of growth factor released per day per mg of particles (n=3).

The particles of Example 1 were assayed in vitro for the release of angiogenic growth factors under conditions approximating in vivo tissue environment. Whereas FGF-2 and VEGF-A release from the particles began immediately, the release of HGF and platelet-derived growth factor (PDGF)-BB were delayed for more than 1 week (FIG. 1b). Further, whereas PDGF-BB release lasted 4 weeks, that of FGF-2, HGF and VEGF-A lasted 6 weeks. In addition, it was confirmed that the growth factors released from the particles retained their full bioactivity using an in vitro assay of cell migration.

The particles of Examples 2 and 3 were also assayed in vitro for the release of angiogenic growth factors under conditions approximating in vivo tissue environment.

FIG. 1c shows that the particles of polysaccharide co-crosslinked with HSA exhibit a first level of release for the first two weeks, higher than the particles of polysaccharides crosslinked without protein.

FIG. 1d shows that alginate particles, co-crosslinked with HSA or not, exhibit similar release rates of HGF, though the release rate of alginate-albumin particles is slightly superior but begins few days later than alginate particles.

FIG. 1e shows that the crosslinking method impacts the release rate of growth factor. Interfacial crosslinking method enables a slow but constant release while transacylation crosslinking method enables a fast but decreasing release.

Example 7

Confocal Imaging of Growth Factor Distribution

To determine the growth factor localization, confocal analyses of particles loaded with fluorescently labeled FGF-2 or HGF were performed.

Twenty μg of rhFGF-2 or rmHGF were fluorescently labeled using an Alexa-555 kit according to the manufacturer's instructions (Microscale protein labeling kit, Invitrogen). Lyophilised particles prepared as described in example 1 were loaded with the fluorescent growth factors, using 1 μg growth factor per mg particles as above. The growth factor-loaded particles were resuspended at 4 mg particles/mL in extracellular fluid mimetic release buffer (EFM-RB, as above). Following over night incubation, the particles were embedded in matrigel, and imaged using a Leica SP5 TCS X inverted confocal microscope at 20×. Images were processed using Leica LAS AF software (version 2.2.0). The results show that both growth factors bound to the microcapsule surface layer, confirming their interactions with the crosslinked protein-polysaccharide membrane. However, FGF-2 was also present in the liquid center of the microcapsule. These findings may in part explain why the particles display different release profiles for FGF-2 and HGF.

Biological Results

Example 8

FGF-2 and HGF Synergistically Stimulate Vascular Cell Migration and Proliferation Cell migration and proliferation: Chemotaxis can be assayed using a modified Boyden migration 48-well chamber (AP48; Neuro Probe Inc., Gaithersburg, USA).

Briefly, membranes are coated with 0.15% gelatin for 1 h at 37° C. Cells, serum starved for 24 h in 1% FCS (without MV bullet kit supplements for HMEC-C and PmT-EC), are stimulated with growth factor for 24 h in the case of pre-treatment using FGF-2 (25 ng/ml for HME, PmT and RAOSMC; 50 ng/ml for HMEC-C) or HGF (25 ng/ml for HMEC-C; 50 ng/ml for HME, PmT and RAOSMC). Next, cells are trypsinized and resuspended in fresh medium supplemented with 0.25% BSA. Into each upper well was added $1 \times 10^4$ cells. The lower wells contained FGF-2 (12.5 ng/ml for HME and RAOSMC; 25 ng/ml for PmT-EC and HMEC-C) or HGF (12.5 ng/ml for HME, PmT-EC, and RAOSMC; 5 ng/ml for HMEC-C). The cells are incubated in the chamber for 6-12 h hours at 37° C., after which cells attached to the membrane are fixed in methanol and stained with Hematoxylin. Six replicate samples are used in each experiment, and experiments are performed at least twice. Migrating cells are analyzed using a light microscope, and reported as numbers of migrating cells per optic field. For analyses of cell proliferation, HME, HMEC-C, and RAOSMCs are either pretreated or not for 24 h with FGF-2 (25 ng/ml for HME; 50 ng/ml for HMEC-C and RAOSMCs) or HGF (25 ng/ml for HMEC-C; 50 ng/ml for HME and RAOSMCs). Next, $1 \times 10^4$ cells are added to each well of 24-well plates and incubated for 2 h at 37° C. After cell attachment, the medium is replaced with fresh medium containing FGF-2 (25 ng/ml for HME; 10 ng/ml for HMEC-C; 50 ng/ml for RAOSMCs) or HGF (1 ng/ml for HME; 25 ng/ml for HMEC-C; 50 ng/ml for RAOSMCs). Cell proliferation is assayed after 24 h, 48 h, or 72 h using the WST-1 assay according to manufacturer's instructions (Roche).

First, it is found that FGF-2 (Fibroblast Growth Factor-2) and HGF (Hepatocyte Growth Factor) synergistically stimulate vascular cell migration and proliferation in vitro, and angiogenesis in vivo.

The effects of FGF-2 and/or HGF are evaluated in vitro using murine heart microvascular endothelial cells (HME), murine embryonic microvascular endothelial cells (PmT-EC), human microvascular cardiac endothelial cells (HMEC-C), and rat aortic smooth muscle cells (SMCs).

Figure 2:
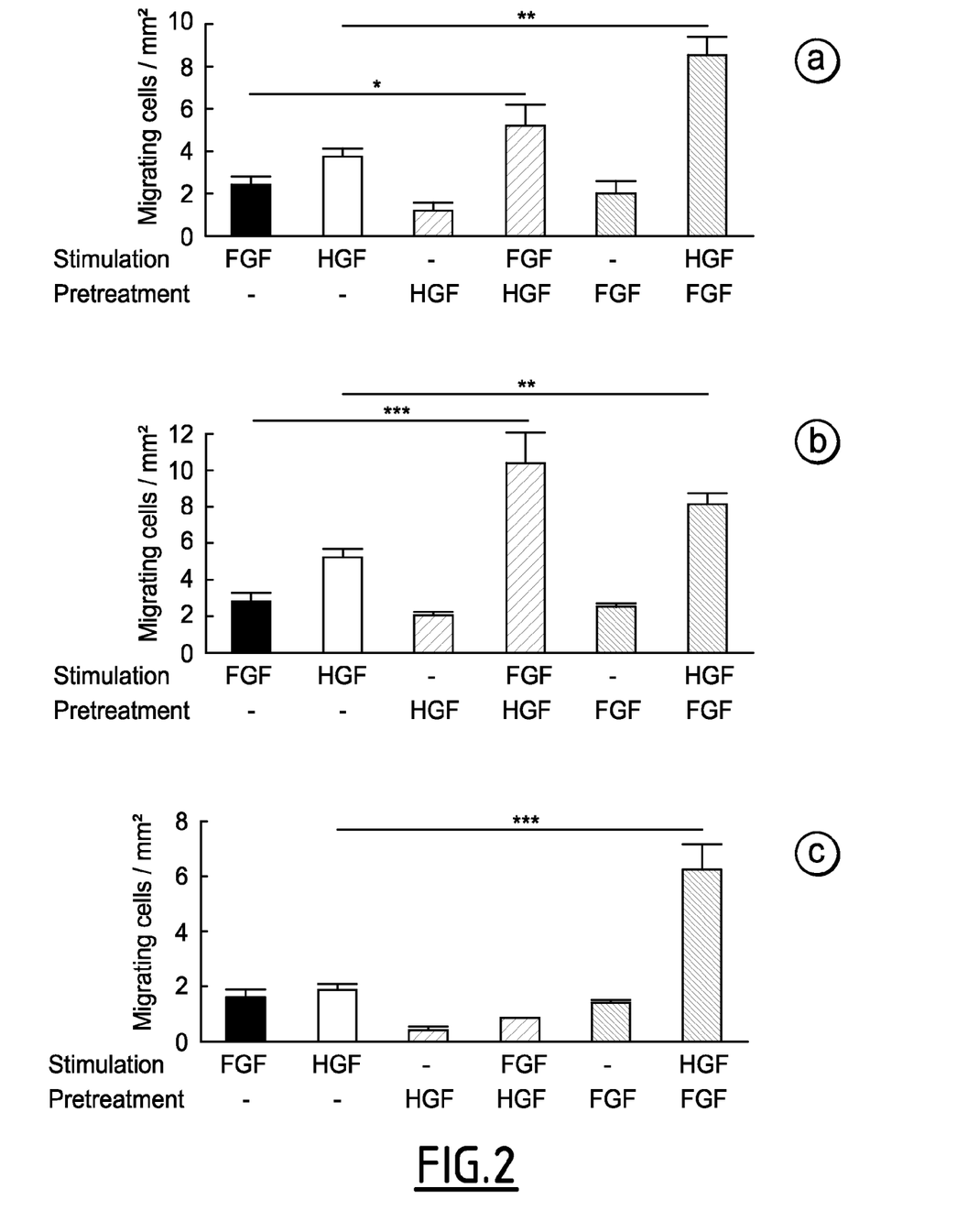
FIG. 2 represents the stimulation of vascular cell migration, synergistically induced by FGF-2 and HGF.
Figure 3:
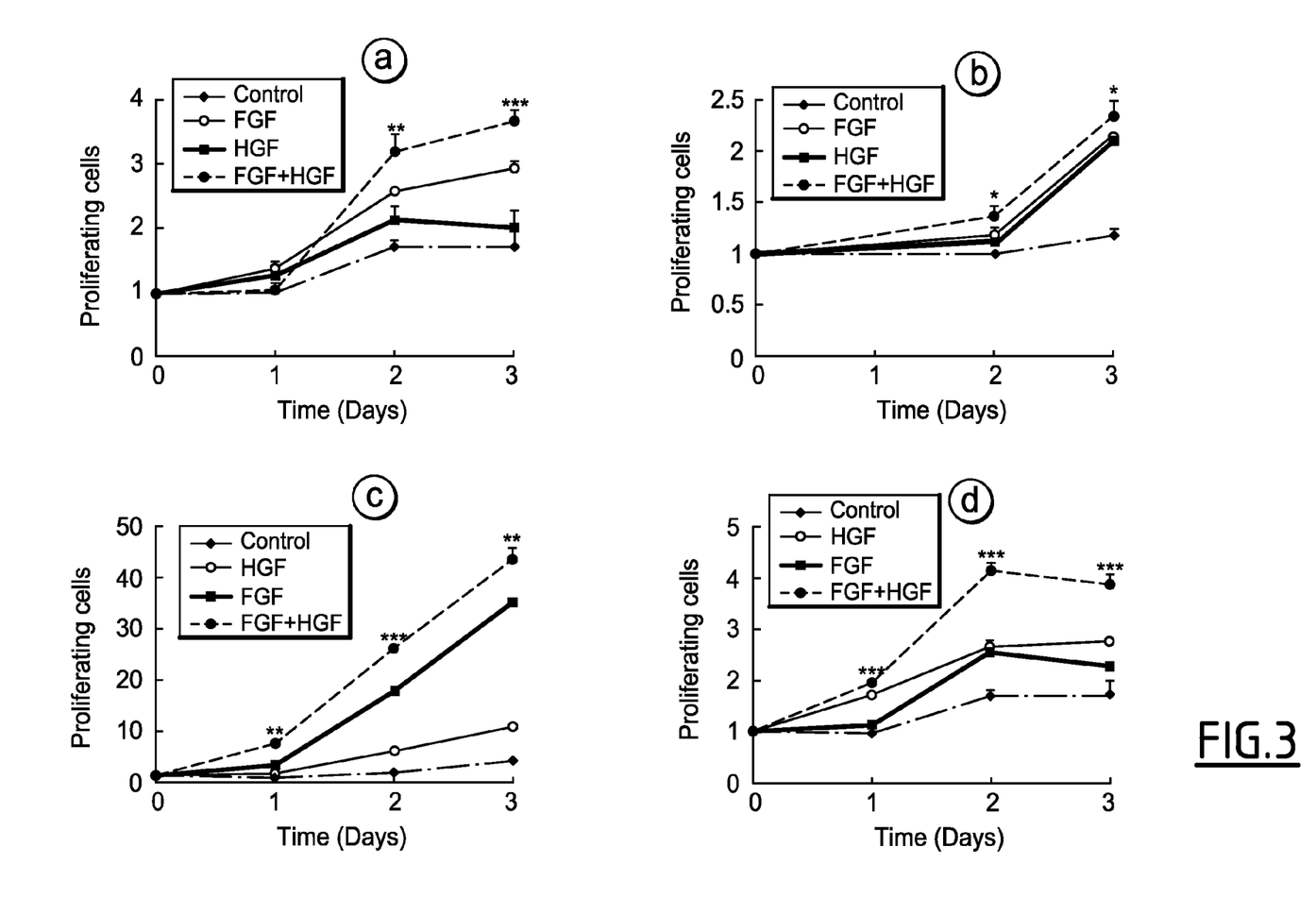
FIG. 3 represents the stimulation of vascular cell proliferation, synergistically induced by FGF-2 and HGF.

Whereas both FGF-2 and HGF used alone induced endothelial cell (EC) and SMC migration (FIG. 2) and proliferation (FIG. 3), HGF pretreatment significantly potentiated EC motility response to FGF-2 (FIG. 2a, 2b).

Correspondingly, pretreatment with FGF-2 enhanced HGF-induced migration (FIG. 2a, 2b). Similarly, in SMCs, FGF-2 strikingly increased motility responses to HGF, although HGF did not alter FGF-2-induced migration (FIG. 2c).

Moreover, pretreatment of HMEC-C (FIG. 3a) or HME (FIG. 3b) with FGF-2 significantly increased HGF-induced cell proliferation. Conversely, pretreatment of HMEC-C (FIG. 3d) or SMCs (FIG. 3c) with HGF significantly increased cell proliferation responses to FGF-2.

These data show that FGF-2 and HGF synergistically stimulate vascular cell migration and proliferation, indicating that the combination of these growth factors may be useful for therapeutic angiogenesis.

Example 9

Effect of Growth Factor Loaded Particles on Angiogenic and Arteriogenic Responses In Vivo (Mouse Matrigel Plug Model)

Growth factor-reduced matrigel (BD, Bedford, Mass., USA) can be used to evaluate angiogenic responses in vivo. Briefly, 500 µL matrigel is mixed with 0.125, 0.5, or 1 mg particles of example 1 loaded with growth factors as above. Controls contained matrigel mixed with buffer or particles without growth factors. The matrigel mixture is subcutaneously injected to form dorsal plugs in male Balb/c mice anesthetized by intraperitoneal injection of ketamine (90 mg/kg, Bayer, France) and xylazine (3.6 mg/kg). After 3 weeks, matrigel plugs are harvested, snap-frozen embedded in Tissue-Tek (Sakura Finetek, Torrance, USA) and stored at −80° C.

Semi-quantitative fluorescence microscopy: Angiogenic growth factor receptor protein expression levels were determined in small and larger blood vessels in histological sections from matrigel plugs implanted with particles loaded with either FGF-2 or HGF, as above. Briefly, 10 µm thick acetone-fixed cryosections were double labeled for either c-Met (rabbit antimouse c-Met, 1:300, sc162, Santa Cruz Biotech, USA) or FGFR-1 (rabbit anti human FGFR1, 1:100, Sigma), in conjunction with CD31 (biotinylated rat anti-mouse CD31, 1:100, BD). Secondary reagents included a donkey antirabbit-Cy3 (1:300, Jackson Immunoresearch Laboratories) and SA-FITC (1:200, Sigma). Following counterstaining with Hoescht's dye (1:10,000) and mounting in Vectashield, the sections were viewed using a Leica SP5 TCS X inverted confocal microscope at 40× (NA=1.25) and images were acquired in a sequential mode. Confocal settings were kept strictly identical between series. In addition; homogeneity of field illumination and power laser output was verified prior to and after experiments to ensure stable conditions of acquisition. Images were analyzed using Bitplane Imaris software (version 6.10) to determine maximal relative levels of signal intensity in regions of interest (ROI) centered on individual blood vessels. In total 3-5 animals per group, and for each animal 5-7 images, each including 7-50 ROI, were analyzed.

To determine if the slow-release system of the invention would influence the angiogenic effect of FGF-2 or HGF in vivo, the comparison of treatment with growth factor-loaded particles versus naked growth factors was studied using the mouse matrigel plug model. Growth factor-delivery by particles was found to be 2-6 times more potent to induce angiogenesis, as compared with bolus delivery of growth factors.

Figure 4:
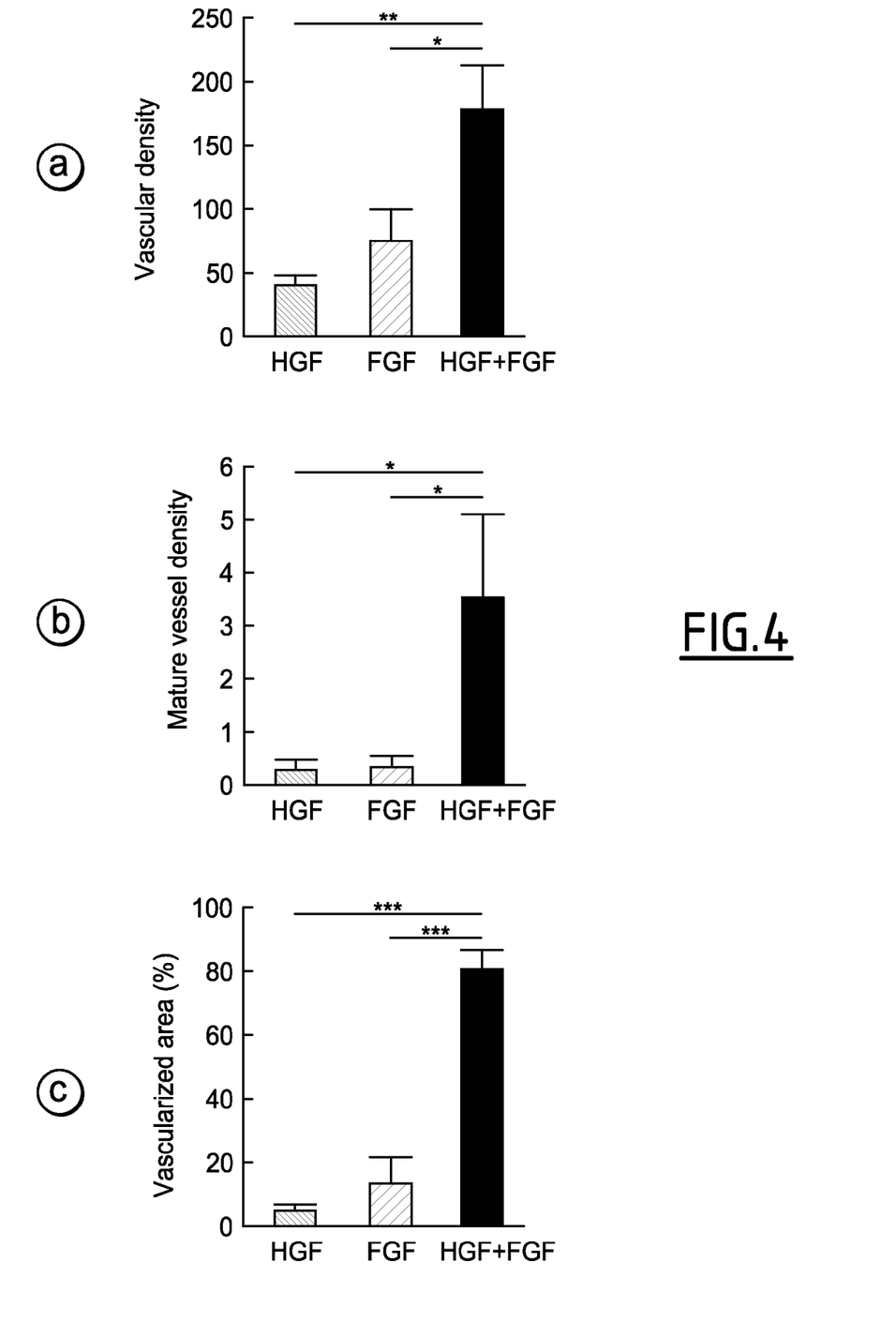
FIG. 4 represents the in vivo angiogenesis and arteriogenesis synergistically induced by the delivery of FGF-2 and HGF via albumin-alginate particles of Example 1.

The reciprocal stimulatory interactions observed between FGF-2 and HGF in vascular cells suggested that these growth factors may cooperatively regulate vessel growth. To investigate this possibility, particles containing FGF-2 and/or HGF were injected in matrigel plugs in mice. In each case, the lowest dose of growth factor resulting in a substantial angiogenic effect was employed. Whereas each growth factor used alone induced a moderate angiogenic response, FGF-2 and HGF used in combination synergistically stimulated angiogenesis and arteriogenesis, as evidenced by the increased vascular density (FIG. 4a), vascular maturity (FIG. 4b), and vascularized area (FIG. 4c) as compared to single growth factor treatments.

Similar results were obtained with particles containing PDGF-BB and/or FGF-2. Whereas each growth factor used alone induced a moderate angiogenic response, PDGF-BB and FGF-2 used in combination synergistically stimulated angiogenesis and arteriogenesis, as evidenced by an increased vascular density, vascular maturity, and vascularized area as compared to single growth factor treatments.

The most potent angiogenic growth factor combination described to date is the association of FGF-2 and PDGF-BB (Cao et al Nat. Med. 2003, 9(5), 604-613). To compare these two different growth factor combinations, particles containing FGF-2 and/or PDGF-BB were injected in matrigel plugs in mice. It was found that whereas the vessel density induced by the combination of FGF-2 and PDGF-BB was moderately greater than that induced by FGF-2 in combination with HGF, the number of mature vessels did not differ.

However, whereas the combination of FGF-2 and PDGF-BB only resulted in 30% of the total plug area being vascularized, the combination of FGF-2 and HGF notably resulted in a matrigel plug vessel content of around 80%.

These results reveal the albumin-alginate particles as particularly efficient for growth factor delivery in vivo. Further, in agreement with the in vitro data, the combination of FGF-2 and HGF synergistically induced angiogenesis and arteriogenesis at a level comparable or surpassing that of the most potent angiogenic growth factor combination currently described.

Example 10

Effect of Growth Factor Loaded Particles after Intramyocardial Injection

Myocardial infarction (MI) was induced in anesthetized (ketamine, 3.6 mg/kg; isoflurane gas, 2%), mechanically ventilated male Wistar rats by ligation of the proximal left coronary artery following a left thoracotomy (n=22 rats/group) as previously described[26, 28]. Rats with infarcts encompassing 20-50% of the left ventricle (LV) were included in the study. Immediately after, particles loaded with growth factors as outlined above were injected in three spots (23 µl/spot) along the infarct border zone on the right anterior side of the LV free wall adjacent to the septum. The total amount of growth factor administered per heart was 125 ng HGF or 500 ng FGF-2 alone or the combination of both. Controls were injected with the same numbers of particles without growth factor. The thorax was closed in three layers and rats allowed to recover on a heating pad before being returned to their cages (2-3 rats/cage). At the time of sacrifice, rats were given a lethal dose of anaesthesia (Sodium Methohexital) followed by rapid excision of the heart through a ventral thoracotomy. Hearts were arrested in diastole by immersion in ice-cold saturated potassium chloride buffer. Lungs and hearts were weighed and the LV dissected before being cut transversally at the level of the papillary muscles and snap-frozen embedded in Tissue-Tek and stored at −80° C.

Histochemistry: MI size and collagen density were determined in 10 µm thick serial heart cryosections fixed in Carnoy's fixative and stained with Sirius Red. Slides were examined and photographed under a light microscope (Zeiss) at 40× magnification. Collagen-rich areas were identified using Image Pro Plus (version 6.3). Collagen content was calculated as percentage of collagen area to total area of the image (n=14-16 animals/group). Infarct size was analyzed in videomicrophotographs of the sections using Adobe Photoshop (CS3 extended version 10) to delineate epicardial and endocardial LV perimeters and infarct perimeter. Infarct size was calculated as: total infarction perimeter/(epicardial LV perimeter+endocardial LV perimeter)×100. For immunohistochemical analyses, 10 μm cryosections were post-fixed in acetone and stained according to standard protocols using rat antimouse CD31 (PECAM-1, 1:100, BD); biotinylated mouse antirat CD31 (PECAM-1, 1:100, BD); mouse antihuman SMA-FITC (smooth muscle a actin, 1:200, Sigma); rabbit anti human Ki67 (1:500, Novocastra Laboratories, Newcastle, UK); and WGA-A488 (wheat germ agglutinin, 1:100, Invitrogen). Secondary reagents included: streptavidin (SA)-Fluoprobe 547 (1:1500, Interchim, France), SA-Cy5 (1:1000, GE Healthcare Life Sciences, Uppsala, Sweden), donkey anti-rabbit Cy3 (1:300, Jackson Immunoresearch Laboratories, Inc., West Grove, USA), or Vectastain® ABC kit containing HRP-conjugated anti-rat IgG (Vector Laboratories, Burlingame, USA) used with DAB substrate kit (Vector Laboratories) for peroxidase staining. Sections were counterstained for 2 min with Hoescht's dye (1:10,000, Sigma). Micrographs (n=2-4 sections/animal, 5-15 animals/group) were captured using 10×, 20× or 40× objectives on a fluorescence microscope (Zeiss Axiolmager Z1) equipped with an Apotome, or using a 2.5× objective on a light microscope (Leica). Images were processed by an operator blinded to the treatment groups using Image Pro-Plus, AxioVision (version 4.6), or Adobe Photoshop image analysis software. Vessel density and vessel maturity were quantified as the number of $CD31^+$ vessels and $SMA^+$ vessels per $mm^2$ respectively. Matrigel plug vessel content was calculated as percentage of vascularized area to total section area. Endothelial proliferation was analyzed by Ki67 and CD31 double labeling, and presented as number of $Ki67^+$ endothelial cells per $mm^2$. Cardiomyocyte sizes were measured in WGA-stained sections. Vessel to cardiomyocyte ratio was calculated as number of vessels to number of cardiomyocytes per $mm^2$.

MRI: Cardiac perfusion was assessed by arterial spin labeling MRI using a 4.7T small animal magnet (Biospec 47/40 advanced II, Brucker, Ettlingen, Germany) equipped with a gradient insert (BGA12S 400 mT/m) and a transmit/recieve radiofrequency coil in quadrature mode with 86 mm internal diameter (Brucker).

Briefly, animals were anesthetized with methohexital and placed in a supine position on a warming cradle. ECG signal were monitored by placing two subcutaneous electrodes on each side of the chest connected to a small animal monitoring and gating system (1025-S-50 model, SA Instruments Inc., NY, USA) for MRI synchronization. After optimization of the radio frequency signal, the perfusion sequence was run in the short-axis plane allowing determination of myocardial tissue perfusion. Global as well as slice-selective spin inversion recovery T1* (fitted time constant) maps were acquired. During acquisition 32 signal averages were performed resulting in an imaging duration of about 20 min per animal[47]. Regional perfusion in the treated area of the LV was calculated as $P=((0.95/T1_{internal})\times(T1^*_{global}/T1^*_{selective})-1)$ of the ROI where $T1_{internal}$ is the signal in the blood[48]. Perfusion images were analyzed with ParaVision 5.0 software (Brucker) by two independent observers.

Echocardiography: Animals (n=15-17 rats/group, and 8 age-matched sham-operated rats) were examined at 1 month and 3 months post-MI by transthoracic echocardiography. 2D images and 2D-guided M-mode, Doppler M mode, and pulsed-wave Doppler recordings were obtained from parasternal short axis (level of papillary muscles) views, using a Vivid 7 Ultrasound (GE Healthcare) echograph with a M12L linear probe operated at 14 MHz, and analyzed using Echopac PC software. LV end-diastolic diameter (EDD) and end-systolic diameter (ESD) were measured by the leading-edge convention, and used to calculate fractional shortening (FS) through the equation FS=[(EDD−ESD)/EDD]×100. Velocity-time integral (VTI) was measured at the level of the pulmonary artery by pulse-wave Doppler. LV free wall AW end-diastolic thickness (AWT ED) and AW end-systolic thickness (AWT ES) were measured in TM mode captured in short-axis views, and used to calculate LV Anterior Wall fractional thickening (AW FT) by the equation AW FT= [(AWT ES−AWT ED)/AWT ED]×100. Rate-corrected Velocity of circumferential shortening (VCFc) was calculated as VCFc=% FS/LVET×(R—R), where LVET=LV ejection time (ms) and R—R=ECG R—R interval. The mean of three consecutive cardiac cycles was used for all measurements in each animal. Measurements, performed by a single echocardiographer blinded to the treatment groups, were made in accordance with the conventions of the American Society of Echocardiography.

Results:

Intramyocardial delivery of FGF-2 and HGF stimulates angiogenesis and arteriogenesis and prevents MI-induced cardiac hypertrophy and fibrosis.

To evaluate the effect of FGF-2 in combination with HGF in a setting of cardiovascular disease, a randomized, blinded experiment in rats surviving coronary artery ligation (n=102) or sham surgery (n=11) was performed.

The experimental MI model leads to the development of CHF within 3 months. Particles of Example 1, loaded or not with FGF-2 and/or HGF, were locally injected in the viable free wall bordering the left ventricular (LV) infarct zone immediately following MI.

At 1 or 3 months post-MI, the angiogenic and arteriogenic cardiac effects were evaluated by immunohistochemistry.

At 1 month post-MI, untreated control rats displayed myocardial vessel rarefaction, including reduced levels of mature blood vessels, as compared with healthy shams. Due to an inherent compensatory angiogenic response, evidenced by increased EC proliferation at 1 month, the total vessel and mature vessel densities were slightly improved in untreated control hearts at 3 months. FGF-2 monotherapy resulted in a further increase in angiogenesis and arteriogenesis locally in the treated LV area, leading to slightly augmented vessel density and significantly increased mature vessel density at 1 month as compared with controls. However, the effects were lost at 3 months.

HGF monotherapy, on the other hand, showing limited arteriogenic effects at 1 month, tended to increase EC proliferation and vascular density at 3 months.

In contrast, the combination therapy induced a potent angiogenic and arteriogenic response, again strictly limited to the treated LV zone, with more than a doubling of the number of proliferating ECs and 3 times more mature blood vessels as compared with untreated controls at 1 month post-MI. Notably, by 3 months, the myocardial vessel density in the combination group had attained normal sham rat levels. Moreover, the mature vessel density in the group treated by FGF-2 and HGF in combination even surpassed that of shams.

Next, the extent of cardiac hypertrophy and fibrosis was evaluated by histological analyses of cardiomyocyte sizes and collagen density respectively. Whereas FGF-2 treatment had no effect on these parameters, both HGF alone and the combination treatment reduced cardiac fibrosis and hypertrophy at 3 months. Notably, the coordinated decrease in cardiomyocyte sizes and increase in blood vessel density generated by the combination treatment resulted in a normalization of the cardiomyocyte:vessel ratio.

Furthermore, as it was observed that therapeutic effects were limited to the injected LV zone, suggesting that the growth factors indeed had been successfully, spatially targeted, the cardiac distribution of the slow-delivery vehicles was verified using fluorescently labeled particles of Example 1. Hearts were evaluated histologically at 6 h, 1 or 2 weeks after intramyocardial injection. The particles were found to be strictly confined to a small area surrounding the three injection points, extending maximally 1-2 mm into the sub-epicardial myocardium. The particles spread over an area representing around 8% of a cross-section the LV at the papillary muscle level after 6 h, progressively decreasing to around 6% after 1 week and 4.5% after 2 weeks.

These findings confirm i) a localized microcapsule distribution centered around the points of injections in agreement with the observed restricted LV effects of the therapies; ii) a comparable timeline of microcapsule degradation in the heart as seen in vitro.

Intramyocardial delivery of FGF-2 and HGF improves regional cardiac perfusion and cardiac function following MI.

To assess if the blood vessels induced by the angiogenic therapies resulted in a functional improvement in cardiac perfusion, magnetic resonance imaging (MRI) was employed.

The results, obtained 3 months post-MI, demonstrate that whereas untreated controls displayed significantly reduced cardiac perfusion compared with healthy sham-operated animals, only the combination treatment increased regional cardiac perfusion in the treated area of the LV.

Next, to investigate whether the multiple beneficial myocardial alterations induced by the angiogenic therapies correlated with improved cardiac function, even though myocardial infarct sizes were similar in all groups, echocardiographic analyses were carried out at 1 and 3 months post-MI.

Untreated controls displayed severe cardiac dysfunction, characterized by LV wall thinning at 1 month, and progressive LV dilation associated with the development of CHF. Both regional and global cardiac contractility were reduced, as evidenced at 1 month by a decreased fractional shortening (FS) and velocity of circumferential fiber shortening (VCFc). HGF monotherapy only slightly improved LV parameters by 3 months, evidenced by decreased LVESD and end-diastolic and systolic volumes and a tendency for increased FS and VCFc as compared with untreated controls. FGF-2 monotherapy, on the other hand, significantly reduced LV dilation, and by 3 months post-MI increased FS and VCFc.

In contrast to these moderate effects of monotherapies, the combination of FGF-2 and HGF reduced LV dilation and LV dysfunction already at 1 month post-MI, as shown by an increased FS and VCFc as compared with untreated controls. This was associated with an increased LV anterior end-systolic wall thickness, and a tendency for increased wall thickening. At 3 months, the combination treatment group displayed a major increase in LV wall thickness and wall thickening as compared with untreated controls and single growth factor groups. Moreover, the LV dilation was further reduced, and associated with a marked recovery of LV function, evidenced by an increased FS and VCFc as compared with both untreated controls and HGF-treated animals, indicating that the development CHF was partially prevented.

Material & Methods
Reagents and Animals

Murine Heart Microvascular Endothelial cells (HME) were a kind gift from Dr Marco Presta (Università di Brescia, Italy). Murine Embryonic Microvascular Endothelial cells (PmT-EC) were a kind gift from Drs. Karin Aase and Lars Holmgren (Karolinska Institutet, Sweden). Primary Human Microvascular Cardiac Endothelial cells (HMEC-C) and Rat Aortic Smooth Muscle Cells (SMC) were purchased from Lonza. All cell lines were maintained in DMEM (Gibco, Invitrogen, Paisley, UK) containing 10% FBS, except PmT-EC and HMEC-C, which were maintained in EGM-2 medium supplemented with MV bullet kit (Lonza). Primary cell cultures were used for experiments between passages 4-8. All cells were maintained at 5% $CO_2$ and 95% air at 37° C. Growth factors, rhFGF-2 (monomer, 157 a.a.), rmHGF (dimer, 463 and 232 a.a.), rhHGF (dimer, 697 a.a.), rhPDGF-BB (dimer, 109 a.a.), were obtained from RnD Systems Inc. (Minnesota, USA). Male Balb/c mice (20-22 g) and male Wistar rats (200-220 g) were purchased from Janvier (Le Genest St Isle, France). Animal experiments were performed in accordance with NIH guidelines, EU regulations, and French National legislation.

Statistics

Data are presented as mean determinants+SEM. Student's t-test (two-tailed) was used to compare two groups of independent samples. For multiple comparisons, one-way analysis of variance (ANOVA) was employed using GraphPad Prism software (version 5.0), followed by Tukey's post-hoc test, except for echocardiographic data where repeated measurements two-way ANOVA was employed followed by Bonferroni post-hoc test. A $p<0.05$ was considered significant.

The invention claimed is:

1. A method of treatment of cardiovascular diseases in a patient in need thereof, comprising administering to said patient a therapeutically effective amount of at least one growth factor,
    wherein said at least one growth factor is released from particles containing a network or a membrane and said at least one growth factor,
    wherein said network or membrane comprises at least one covalently cross-linked polysaccharide and a protein,
    wherein said protein is co-cross-linked with the at least one covalently cross-linked polysaccharide,
    wherein said at least one growth factor is adsorbed by electrostatic interactions to the at least one covalently cross-linked polysaccharide,
    wherein the polysaccharide is selected from the group consisting of acacia gum, alginic acid and derivatives thereof, alginic salts, alginic esters, chondroitin-4-sulfate, chondroitin-6-sulfate, and mixtures thereof,
    wherein the protein is selected from the group consisting of albumins, said therapeutically effective amount being administered by injection into a tissue of the patient,
    and wherein the particles provide sustained release of the growth factor over a period of at least 15 days.

2. The method according to claim 1, wherein the growth factor is selected from the group consisting of fibroblast growth factors (FGFs), hepatocyte growth factor (HGF), platelet derived growth factors (PDGFs), vascular endothelial growth factors (VEGFs), angiopoietins (Angs), granulocyte colony-stimulating factor (GCSF), transforming growth factors (TGFs), placental growth factors (PlGFs), epidermal growth factor (EGF), stromal derived growth factor (SDF-1), insulin-like growth factors (IGFs), nerve growth factor (NGF), osteogenin, or hormones, and mixtures thereof.

3. The method according to claim 1, wherein the at least one growth factor is at least two growth factors.

4. The method according to claim 1, wherein a diameter of each of said particles ranges from 5 μm to 1,000 μm.

5. The method according to claim 1, wherein the particles have a core/membrane structure wherein:
the membrane comprises the at least one covalently cross-linked polysaccharide and the at least one growth factor adsorbed on the at least one covalently cross-linked polysaccharide, and
the core is liquid.

6. The method according to claim 1, wherein the particles have a matrix structure formed of a said network comprising the at least one covalently cross-linked polysaccharide, the protein co-cross-linked with the at least one covalently cross-linked polysaccharide, and the at least one growth factor adsorbed by electrostatic interactions on the at least one covalently cross-linked polysaccharide, said network filling the whole volume of the particles and having pores wherein an aqueous solution is entrapped.

7. The method of claim 1, wherein said at least one growth factor is adsorbed by electrostatic interactions to the at least one covalently cross-linked polysaccharide at a surface of said particles.

8. The method of claim 1, wherein said at least one growth factor includes FGF2 and HGF.

9. The method of claim 1, wherein said step of administering results in spatially targeted delivery of said at least one growth factor to an injection zone.

10. The method of claim 1, wherein said particle contains said network and said network is present throughout the whole volume of the particle.

11. The method of claim 1, wherein said particle contains said membrane and said membrane surrounds a liquid core within said particle.

12. The method of claim 1, wherein said particles are growth factor delivery systems delivering a combination of growth factor with different kinetics.

13. The method of claim 12, wherein said combination of growth factors includes one or more of FGF-2, HGF, PDGF-BB, and VEGF-A.

* * * * *